(12) United States Patent
Hilleli et al.

(10) Patent No.: US 12,426,934 B2
(45) Date of Patent: Sep. 30, 2025

(54) CRYOGEN FLOW CONTROL

(71) Applicant: ICECURE MEDICAL LTD., Caesarea (IL)

(72) Inventors: Ron Hilleli, Zichron Yaacov (IL); Shai Kaufman, Nir Eliyahu (IL); Naum Muchnik, Yokneam Illit (IL)

(73) Assignee: IceCure Medical Ltd., Caesarea (IL)

( * ) Notice: Subject to any disclaimer, the term of this patent is extended or adjusted under 35 U.S.C. 154(b) by 664 days.

(21) Appl. No.: 17/681,868

(22) Filed: Feb. 28, 2022

(65) Prior Publication Data

US 2023/0270483 A1 Aug. 31, 2023

(51) Int. Cl.
*A61B 18/12* (2006.01)
*A61B 18/02* (2006.01)
*A61B 18/00* (2006.01)

(52) U.S. Cl.
CPC .... *A61B 18/02* (2013.01); *A61B 2018/00648* (2013.01); *A61B 2018/00666* (2013.01);
(Continued)

(58) Field of Classification Search
CPC .......... A61B 18/02; A61B 2018/00333; A61B 2018/00642; A61B 2018/00648; A61B 2018/00666; A61B 2018/00714; A61B 2018/00744; A61B 2018/00791; A61B 2018/00863; A61B 2018/0262; A61B 2018/0268; A61B 2090/064
See application file for complete search history.

(56) References Cited

U.S. PATENT DOCUMENTS 2,319,542 A   5/1943  Hall
2,888,879 A   6/1959  Gaarder
(Continued)

FOREIGN PATENT DOCUMENTS

CH        265929 A    12/1949
CN      101803947 B    9/2012
(Continued)

OTHER PUBLICATIONS

U.S. Appl. No. 17/866,614 Office Action dated Feb. 29, 2024.
(Continued)

*Primary Examiner* — Tigist S Demie
(74) *Attorney, Agent, or Firm* — Meitar Patents Ltd.; Daniel Kligler (57) ABSTRACT

Apparatus, including a probe, containing a first lumen and a second lumen and having a distal end that contacts tissue of a living subject. A fluid supply delivers a cryogenic fluid through the first lumen to the distal end and receives cryogenic fluid returning via the second lumen. A temperature sensor is located at the distal end. A pressure sensor located at a proximal end of the first lumen measures a pressure of the cryogenic fluid. A processor controls a delivery rate of the cryogenic fluid from the fluid supply, so that, when a temperature measured by the temperature sensor is less than a preset guard temperature, the delivery state is a preset low rate, and when the temperature measured by the temperature sensor is greater than or equal to the preset guard temperature, the delivery rate is set in response to a pressure measured by the pressure sensor.

26 Claims, 5 Drawing Sheets

(52) U.S. Cl.
CPC ............ *A61B 2018/00744* (2013.01); *A61B 2018/00791* (2013.01); *A61B 2018/0262* (2013.01)

(56) References Cited

U.S. PATENT DOCUMENTS

| | | | |
|---|---|---|---|
| 3,234,746 A | 2/1966 | Smith |
| 3,358,472 A | 12/1967 | Kipling |
| 3,456,595 A | 7/1969 | Gottzmann et al. |
| 3,664,344 A | 5/1972 | Bryne |
| 3,696,813 A | 10/1972 | Wallach |
| 3,699,775 A | 10/1972 | Cowans |
| 3,712,306 A | 1/1973 | Bryne |
| 3,736,936 A | 6/1973 | Basiulis |
| 3,736,937 A | 6/1973 | Basilius |
| 3,800,552 A | 4/1974 | Sollami |
| 3,845,974 A | 11/1974 | Pelloux-Gervais |
| 3,862,630 A | 1/1975 | Balamuth |
| 3,882,849 A | 5/1975 | Smith |
| 3,938,505 A | 2/1976 | Jamshidi |
| 3,958,443 A | 5/1976 | Berrettini |
| 3,971,383 A | 7/1976 | Van Gerven |
| 3,988,029 A | 10/1976 | Gibson |
| 4,082,096 A | 4/1978 | Benson |
| 4,091,634 A | 5/1978 | Shepherd |
| 4,107,946 A | 8/1978 | Potter |
| 4,127,903 A | 12/1978 | Schachar |
| 4,200,104 A | 4/1980 | Harris |
| 4,202,336 A | 5/1980 | Van Gerven |
| 4,211,231 A | 7/1980 | Rzasa |
| 4,279,626 A | 7/1981 | Buchmuller |
| 4,306,568 A | 12/1981 | Torre |
| 4,313,306 A | 2/1982 | Torre |
| 4,367,744 A | 1/1983 | Sole |
| 4,376,376 A | 3/1983 | Gregory |
| 4,428,748 A | 1/1984 | Peyman |
| 4,463,458 A | 8/1984 | Seidner |
| 4,481,948 A | 11/1984 | Sole |
| 4,487,253 A | 12/1984 | Malek |
| 4,541,457 A | 9/1985 | Blenkush |
| 4,545,367 A | 10/1985 | Tucci |
| 4,552,208 A | 11/1985 | Sorenson |
| 4,570,626 A | 2/1986 | Norris |
| 4,573,525 A | 3/1986 | Boyd |
| 4,611,654 A | 9/1986 | Buchsel |
| 4,613,112 A | 9/1986 | Phlipot et al. |
| 4,617,018 A | 10/1986 | Nishi |
| 4,676,225 A | 6/1987 | Bartera |
| 4,724,834 A | 2/1988 | Alperovich et al. |
| 4,726,194 A | 2/1988 | Mackay |
| 4,765,396 A | 8/1988 | Seidenberg |
| 4,770,171 A | 9/1988 | Sweren |
| 4,802,475 A | 2/1989 | Weshahy |
| 4,823,790 A | 4/1989 | Alperovich et al. |
| 4,831,856 A | 5/1989 | Gano |
| 4,832,022 A | 5/1989 | Tjulkov et al. |
| 4,946,460 A | 8/1990 | Merry |
| 5,026,387 A | 6/1991 | Thomas |
| 5,047,043 A | 9/1991 | Kubota |
| 5,108,390 A | 4/1992 | Potocky |
| 5,147,355 A | 9/1992 | Friedman |
| 5,188,102 A | 2/1993 | Idemoto |
| 5,214,925 A | 6/1993 | Hoy |
| 5,222,937 A | 6/1993 | Kagawa |
| 5,224,943 A | 7/1993 | Goddard |
| 5,243,826 A | 9/1993 | Longsworth |
| 5,254,082 A | 10/1993 | Takase |
| 5,254,116 A | 10/1993 | Baust |
| 5,261,923 A | 11/1993 | Soares |
| 5,263,957 A | 11/1993 | Davison |
| 5,264,116 A | 11/1993 | Apelian |
| 5,267,960 A | 12/1993 | Hayman et al. |
| 5,275,595 A | 1/1994 | Dobak |
| 5,281,215 A | 1/1994 | Milder |
| 5,295,484 A | 3/1994 | Marcus |
| 5,324,286 A | 6/1994 | Fowle |
| 5,330,745 A | 7/1994 | Mcdow |
| 5,334,181 A | 8/1994 | Rubinsky |
| 5,342,380 A | 8/1994 | Hood |
| 5,361,591 A | 11/1994 | Caldwell |
| 5,363,879 A | 11/1994 | Rhoades |
| 5,391,144 A | 2/1995 | Sakurai |
| 5,411,374 A | 5/1995 | Gram |
| 5,417,073 A | 5/1995 | James |
| 5,423,807 A | 6/1995 | Milder |
| 5,429,138 A | 7/1995 | Jamshidi |
| 5,429,155 A | 7/1995 | Brzyski et al. |
| 5,438,837 A | 8/1995 | Caldwell |
| 5,441,512 A | 8/1995 | Muller |
| 5,445,462 A | 8/1995 | Johnson |
| 5,452,582 A | 9/1995 | Longsworth |
| 5,488,831 A | 2/1996 | Griswold |
| 5,516,505 A | 5/1996 | Mcdow |
| 5,520,682 A | 5/1996 | Baust |
| 5,522,870 A | 6/1996 | Ben-Zion |
| 5,526,821 A | 6/1996 | Jamshidi |
| 5,547,473 A | 8/1996 | Peyman |
| 5,573,532 A | 11/1996 | Chang |
| 5,600,143 A | 2/1997 | Roberts |
| 5,603,221 A | 2/1997 | Maytal |
| 5,616,838 A | 4/1997 | Preston et al. |
| 5,620,479 A | 4/1997 | Diederich |
| 5,632,743 A | 5/1997 | Clarke |
| 5,647,868 A | 7/1997 | Chinn |
| 5,654,279 A | 8/1997 | Rubinsky |
| 5,658,276 A | 8/1997 | Griswold |
| 5,674,218 A | 10/1997 | Rubinsky |
| 5,683,592 A | 11/1997 | Bartholomew |
| 5,687,776 A | 11/1997 | Forgash |
| 5,716,353 A | 2/1998 | Matsuura |
| 5,720,743 A | 2/1998 | Bischof |
| 5,728,130 A | 3/1998 | Ishikawa |
| 5,735,845 A | 4/1998 | Zupkas |
| 5,771,946 A | 6/1998 | Kooy |
| 5,787,940 A | 8/1998 | Bonn |
| 5,800,448 A | 9/1998 | Banko |
| 5,800,487 A | 9/1998 | Mikus |
| 5,814,040 A | 9/1998 | Nelson |
| 5,860,970 A | 1/1999 | Goddard et al. |
| 5,860,971 A | 1/1999 | Clarke |
| 5,868,673 A | 2/1999 | Vesely |
| 5,885,276 A | 3/1999 | Ammar |
| 5,899,897 A | 5/1999 | Rabin |
| 5,906,612 A | 5/1999 | Chinn |
| 5,906,628 A | 5/1999 | Miyawaki |
| 5,910,104 A | 6/1999 | Dobak |
| 5,921,982 A | 7/1999 | Lesh |
| 5,935,124 A | 8/1999 | Klumb et al. |
| 5,946,920 A | 9/1999 | Clarke |
| 5,957,918 A | 9/1999 | Griswold |
| 5,976,092 A | 11/1999 | Chinn |
| 5,976,505 A | 11/1999 | Henderson |
| 5,992,158 A | 11/1999 | Goddard |
| 6,007,571 A | 12/1999 | Neilson et al. |
| 6,012,453 A | 1/2000 | Tsais |
| 6,024,750 A | 2/2000 | Mastri |
| 6,027,499 A | 2/2000 | Johnston et al. |
| 6,032,068 A | 2/2000 | Daniel |
| 6,032,675 A | 3/2000 | Rubinsky |
| 6,035,646 A | 3/2000 | Griswold |
| 6,035,657 A | 3/2000 | Dobak |
| 6,036,667 A | 3/2000 | Manna |
| 6,039,730 A | 3/2000 | Rabin |
| 6,041,787 A | 3/2000 | Rubinsky |
| 6,042,342 A | 3/2000 | Orian |
| 6,053,906 A | 4/2000 | Honda |
| 6,059,820 A | 5/2000 | Baronov |
| 6,063,098 A | 5/2000 | Houser |
| 6,074,412 A | 6/2000 | Mikus et al. |
| 6,082,400 A | 7/2000 | Tocha |
| 6,095,149 A | 8/2000 | Sharkey |
| 6,123,675 A | 9/2000 | Kreizman et al. |
| 6,142,991 A | 11/2000 | Schatzberger |
| 6,145,322 A | 11/2000 | Odashima |

(56) References Cited

U.S. PATENT DOCUMENTS

| | | |
|---|---|---|
| 6,152,894 A | 11/2000 | Kubler |
| 6,182,666 B1 | 2/2001 | Dobak |
| 6,183,019 B1 | 2/2001 | Owen |
| 6,190,378 B1 | 2/2001 | Jarvinen |
| 6,200,308 B1 | 3/2001 | Pope |
| 6,203,288 B1 | 3/2001 | Kottke |
| 6,206,832 B1 | 3/2001 | Downey |
| 6,212,904 B1 | 4/2001 | Arkharov |
| 6,216,029 B1 | 4/2001 | Paltieli |
| 6,235,018 B1 | 5/2001 | LePivert |
| 6,235,019 B1 | 5/2001 | Lehmann et al. |
| 6,237,355 B1 | 5/2001 | Li |
| 6,251,105 B1 | 6/2001 | Mikus |
| 6,270,494 B1 | 8/2001 | Kovalcheck |
| 6,280,407 B1 | 8/2001 | Manna |
| 6,354,088 B1 | 3/2002 | Emmer |
| 6,355,033 B1 | 3/2002 | Moorman |
| 6,358,264 B2 | 3/2002 | Banko |
| 6,379,348 B1 | 4/2002 | Onik |
| 6,383,180 B1 | 5/2002 | Lalonde |
| 6,383,181 B1 | 5/2002 | Johnston |
| 6,411,852 B1 | 6/2002 | Danek |
| 6,413,263 B1 | 7/2002 | Lobdill |
| 6,423,009 B1 | 7/2002 | Downey |
| 6,432,102 B2 | 8/2002 | Joye |
| 6,457,212 B1 | 10/2002 | Craig |
| 6,468,268 B1 | 10/2002 | Abboud |
| 6,468,269 B1 | 10/2002 | Korpan |
| 6,471,217 B1 | 10/2002 | Hayfield |
| 6,471,694 B1 | 10/2002 | Kudaravalli et al. |
| 6,482,178 B1 | 11/2002 | Andrews |
| 6,497,714 B1 | 12/2002 | Ishikawa |
| 6,500,109 B2 | 12/2002 | Tokita |
| 6,500,172 B1 | 12/2002 | Panescu et al. |
| 6,503,246 B1 | 1/2003 | Har-Shai |
| 6,505,629 B1 | 1/2003 | Mikus et al. |
| 6,508,814 B2 | 1/2003 | Tortal |
| 6,513,336 B2 | 2/2003 | Zurecki |
| 6,547,784 B1 | 4/2003 | Thompson |
| 6,551,309 B1 | 4/2003 | LePivert |
| 6,562,030 B1 | 5/2003 | Abboud |
| 6,565,556 B1 | 5/2003 | Korpan |
| 6,581,390 B2 | 6/2003 | Emmer |
| 6,582,425 B2 | 6/2003 | Simpson |
| 6,582,426 B2 | 6/2003 | Moorman |
| 6,631,615 B2 | 10/2003 | Drube |
| 6,640,556 B2 | 11/2003 | Ursan |
| 6,659,730 B2 | 12/2003 | Gram |
| 6,659,956 B2 | 12/2003 | Barzell |
| 6,672,095 B1 | 1/2004 | Luo |
| 6,678,621 B2 | 1/2004 | Wiener |
| 6,682,525 B2 | 1/2004 | Lalonde |
| 6,698,423 B1 | 3/2004 | Honkonen |
| 6,702,761 B1 | 3/2004 | Damadian |
| 6,706,037 B2 | 3/2004 | Zvuloni et al. |
| 6,761,715 B2 | 7/2004 | Carroll |
| 6,765,333 B1 | 7/2004 | Mariaucue |
| 6,768,917 B1 | 7/2004 | Van Vaals |
| 6,772,766 B2 | 8/2004 | Gallo |
| 6,786,902 B1 | 9/2004 | Rabin |
| 6,789,545 B2 | 9/2004 | Littrup et al. |
| 6,824,543 B2 | 11/2004 | Lentz |
| 6,852,110 B2 | 2/2005 | Roy et al. |
| 6,852,706 B1 | 2/2005 | Heber-Katz |
| 6,858,025 B2 | 2/2005 | Maurice |
| 6,866,624 B2 | 3/2005 | Chornenky et al. |
| 6,869,439 B2 | 3/2005 | White |
| 6,889,695 B2 | 5/2005 | Pankratov |
| 6,898,940 B2 | 5/2005 | Gram |
| 6,908,472 B2 | 6/2005 | Wiener |
| 6,910,510 B2 | 6/2005 | Gale |
| 6,913,604 B2 | 7/2005 | Mihalik |
| 6,918,869 B2 | 7/2005 | Shaw et al. |
| 6,929,639 B2 | 8/2005 | Lafontaine |
| 6,932,771 B2 | 8/2005 | Whitmore |
| 6,936,045 B2 | 8/2005 | Yu |
| 6,939,346 B2 | 9/2005 | Kannenberg et al. |
| 6,942,659 B2 | 9/2005 | Lehmann |
| 6,945,477 B2 | 9/2005 | Lambert et al. |
| 6,951,569 B2 | 10/2005 | Nohilly |
| 6,954,977 B2 | 10/2005 | Maguire |
| 6,995,493 B2 | 2/2006 | Isoda |
| 7,001,378 B2 | 2/2006 | Yon |
| 7,025,762 B2 | 4/2006 | Johnston |
| 7,025,767 B2 | 4/2006 | Schaefer |
| 7,071,690 B2 | 7/2006 | Butts |
| 7,081,111 B2 | 7/2006 | Svaasand |
| 7,083,612 B2 | 8/2006 | Littrup et al. |
| 7,101,367 B2 | 9/2006 | Xiao |
| 7,128,347 B2 | 10/2006 | Kerin |
| 7,128,738 B2 | 10/2006 | Littrup et al. |
| 7,128,739 B2 | 10/2006 | Prakash |
| 7,137,978 B2 | 11/2006 | Levin |
| 7,144,228 B2 | 12/2006 | Emmer |
| 7,151,374 B2 | 12/2006 | Doty |
| 7,156,840 B2 | 1/2007 | Lentz et al. |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,192,426 B2 | 3/2007 | Baust et al. |
| 7,207,985 B2 | 4/2007 | Duong |
| 7,213,400 B2 | 5/2007 | Dickerson |
| 7,223,080 B2 | 5/2007 | Duron |
| 7,250,046 B1 | 7/2007 | Fallat |
| 7,252,648 B2 | 8/2007 | Honda |
| 7,255,693 B1 | 8/2007 | Johnston |
| 7,273,479 B2 | 9/2007 | Littrup |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Yon |
| 7,318,327 B2 | 1/2008 | Dickerson |
| 7,344,530 B2 | 3/2008 | Bischof |
| 7,344,531 B2 | 3/2008 | Bischof |
| 7,354,434 B2 | 4/2008 | zvuloni |
| 7,357,797 B2 | 4/2008 | Ryba |
| 7,361,187 B2 | 4/2008 | Duong |
| 7,381,207 B2 | 6/2008 | Duong |
| 7,407,501 B2 | 8/2008 | Zvuloni |
| 7,422,583 B2 | 9/2008 | Maurice |
| 7,425,211 B2 | 9/2008 | Levin et al. |
| 7,458,379 B2 | 12/2008 | Littrup et al. |
| 7,458,968 B2 | 12/2008 | Carroll |
| 7,469,718 B2 | 12/2008 | Lambert et al. |
| 7,481,806 B2 | 1/2009 | Levin |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 7,568,735 B2 | 8/2009 | Akiba |
| 7,731,711 B2 | 6/2010 | Levin |
| 7,780,657 B2 | 8/2010 | Abboud et al. |
| 7,803,154 B2 | 9/2010 | Toubia et al. |
| 7,921,657 B2 | 4/2011 | Littrup et al. |
| 7,938,822 B1 | 5/2011 | Berzak et al. |
| 7,967,814 B2 | 6/2011 | Levin |
| 7,967,815 B1 | 6/2011 | Berzak et al. |
| 8,080,005 B1 | 12/2011 | Berzak et al. |
| 8,092,448 B2 | 1/2012 | DeLonzor |
| 8,162,812 B2 | 4/2012 | Shai et al. |
| 8,187,264 B2 | 5/2012 | Kobayashi |
| 8,348,855 B2 | 1/2013 | Hillely et al. |
| 8,418,480 B2 | 4/2013 | Danley et al. |
| 8,475,448 B2 | 7/2013 | Sharareh et al. |
| 8,500,173 B2 | 8/2013 | Zahler et al. |
| 8,517,749 B2 | 8/2013 | Marshall |
| 8,551,081 B2 | 10/2013 | Baust et al. |
| 8,579,892 B2 | 11/2013 | Hoey et al. |
| 8,591,505 B2 | 11/2013 | Sharon et al. |
| 8,671,700 B2 | 3/2014 | Duong et al. |
| 8,685,014 B2 | 4/2014 | Babkin et al. |
| 8,709,005 B2 | 4/2014 | Berzak et al. |
| 8,784,409 B2 | 7/2014 | Robilotto et al. |

(56) References Cited

U.S. PATENT DOCUMENTS

| | | |
|---|---|---|
| 8,814,850 B2 | 8/2014 | Babkin et al. |
| 8,845,628 B2 | 9/2014 | Babkin et al. |
| 8,906,004 B2 | 12/2014 | Berzak et al. |
| 8,998,888 B2 | 4/2015 | Baust et al. |
| 9,039,689 B2 | 5/2015 | Berzak et al. |
| 9,050,072 B2 | 6/2015 | Delonzor et al. |
| 9,050,075 B2 | 6/2015 | Berzak et al. |
| 9,101,343 B2 | 8/2015 | Duong et al. |
| 9,125,689 B2 | 9/2015 | Mielekamp |
| 9,144,461 B2 | 9/2015 | Kruecker et al. |
| 9,157,560 B2 | 10/2015 | Rehder et al. |
| 9,237,919 B2 | 1/2016 | Maschke |
| 9,316,215 B2 | 4/2016 | Mackey |
| 9,408,654 B2 | 8/2016 | Baust et al. |
| 9,441,997 B2 | 9/2016 | Downie et al. |
| 9,808,302 B2 | 11/2017 | Berzak et al. |
| 9,956,024 B2 | 5/2018 | Mahrouche et al. |
| 10,022,175 B2 | 7/2018 | Abboud et al. |
| 10,054,262 B2 | 8/2018 | Baust et al. |
| 10,098,685 B2 | 10/2018 | Lalonde et al. |
| 10,125,771 B2 | 11/2018 | Caldwell et al. |
| 10,159,522 B2 | 12/2018 | Littrup et al. |
| 10,213,244 B2 | 2/2019 | Fourkas et al. |
| 10,363,081 B2 | 7/2019 | Clarke |
| 10,383,686 B2 | 8/2019 | Panescu et al. |
| 10,390,871 B2 | 8/2019 | Ramadhyani et al. |
| 10,485,602 B2 | 11/2019 | Geiselhart |
| 10,531,656 B2 | 1/2020 | Schryver |
| 10,702,251 B2 | 7/2020 | Nevo |
| 10,828,080 B2 | 11/2020 | George et al. |
| 10,859,211 B2 | 12/2020 | Bollinger |
| 11,026,737 B2 | 6/2021 | Baust et al. |
| 11,060,778 B2 | 7/2021 | Jankowsky et al. |
| 11,266,458 B2 | 3/2022 | Perron et al. |
| 11,413,085 B2 | 8/2022 | Snyder et al. |
| 2001/0047129 A1 | 11/2001 | Hall |
| 2002/0016540 A1 | 2/2002 | Mikus |
| 2002/0022832 A1 | 2/2002 | Mikus |
| 2002/0040220 A1 | 4/2002 | Zvuloni |
| 2002/0042609 A1 | 4/2002 | Kelman et al. |
| 2002/0077654 A1 | 6/2002 | Javier |
| 2002/0085921 A1 | 7/2002 | Gram |
| 2002/0144509 A1 | 10/2002 | Chalk |
| 2002/0156469 A1 | 10/2002 | Yon |
| 2002/0157402 A1 | 10/2002 | Drube |
| 2002/0160640 A1 | 10/2002 | Korpan |
| 2002/0161385 A1 | 10/2002 | Wiener |
| 2003/0060762 A1 | 3/2003 | Zvuloni |
| 2003/0079480 A1 | 5/2003 | Emmer |
| 2003/0126867 A1 | 7/2003 | Drube |
| 2003/0135119 A1 | 7/2003 | Lee |
| 2003/0181897 A1 | 9/2003 | Thomas |
| 2003/0220635 A1 | 11/2003 | Knowlton |
| 2004/0024391 A1 | 2/2004 | Cytron |
| 2004/0024392 A1 | 2/2004 | Lewis et al. |
| 2004/0055316 A1 | 3/2004 | Emmer |
| 2004/0078033 A1 | 4/2004 | Levin |
| 2004/0106841 A1 | 6/2004 | Shaw et al. |
| 2004/0210212 A1 | 10/2004 | Maurice |
| 2004/0215178 A1 | 10/2004 | Maurice |
| 2005/0016185 A1 | 1/2005 | Emmer |
| 2005/0038422 A1 | 2/2005 | Maurice |
| 2005/0043725 A1 | 2/2005 | Duong et al. |
| 2005/0056027 A1 | 3/2005 | White |
| 2005/0086949 A1 | 4/2005 | Noble |
| 2005/0106153 A1 | 5/2005 | Nordouist |
| 2005/0159735 A1 | 7/2005 | Walton et al. |
| 2005/0177147 A1 | 8/2005 | Vancelette |
| 2005/0192564 A1 | 9/2005 | Cosman |
| 2005/0198972 A1 | 9/2005 | Entz et al. |
| 2005/0214268 A1 | 9/2005 | Cavanagh |
| 2005/0274127 A1 | 12/2005 | Drube et al. |
| 2005/0274142 A1 | 12/2005 | Corey |
| 2005/0288658 A1 | 12/2005 | Littrup et al. |
| 2006/0049274 A1 | 3/2006 | Hume |
| 2006/0053165 A1 | 3/2006 | Hume |
| 2006/0079867 A1 | 4/2006 | Berzak |
| 2006/0100495 A1 | 5/2006 | Santoianni et al. |
| 2006/0122590 A1 | 6/2006 | Bliweis |
| 2006/0155267 A1 | 7/2006 | Berzak |
| 2006/0155268 A1 | 7/2006 | Amir |
| 2006/0253114 A1 | 11/2006 | Saadat |
| 2006/0264920 A1 | 11/2006 | Duong |
| 2006/0293647 A1 | 12/2006 | McRae |
| 2007/0000259 A1 | 1/2007 | Brook |
| 2007/0043342 A1 | 2/2007 | Kleinberger |
| 2007/0088217 A1 | 4/2007 | Babaev |
| 2007/0093710 A1 | 4/2007 | Maschke |
| 2007/0123815 A1 | 5/2007 | Mark |
| 2007/0129626 A1 | 6/2007 | Mahesh |
| 2007/0129629 A1 | 6/2007 | Beauregard |
| 2007/0149959 A1 | 6/2007 | DeLonzor |
| 2007/0153969 A1 | 7/2007 | Maschke |
| 2007/0166171 A1 | 7/2007 | Kondo |
| 2007/0167939 A1 | 7/2007 | Duong |
| 2007/0244474 A1 | 10/2007 | DeLonzor et al. |
| 2007/0276360 A1 | 11/2007 | Johnston |
| 2007/0277550 A1 | 12/2007 | Li et al. |
| 2008/0027419 A1 | 1/2008 | Hamel |
| 2008/0039745 A1 | 2/2008 | Babaev |
| 2008/0051774 A1 | 2/2008 | Ofir |
| 2008/0051776 A1 | 2/2008 | Bliweis |
| 2008/0097251 A1 | 4/2008 | Babaev |
| 2008/0114344 A1 | 5/2008 | Xiao et al. |
| 2008/0114346 A1 | 5/2008 | Levin et al. |
| 2008/0115509 A1 | 5/2008 | Gullickson |
| 2008/0119834 A1 | 5/2008 | Vancelette |
| 2008/0119838 A1 | 5/2008 | Vancelette |
| 2008/0125764 A1 | 5/2008 | Vancelette et al. |
| 2008/0140061 A1 | 6/2008 | Toubia et al. |
| 2008/0319433 A1 | 12/2008 | Geiselhart |
| 2009/0011032 A1 | 1/2009 | LePivert |
| 2009/0149957 A1 | 6/2009 | Ross et al. |
| 2009/0163902 A1 | 6/2009 | DeLonzor et al. |
| 2009/0182320 A1 | 7/2009 | DeLonzor et al. |
| 2009/0192505 A1 | 7/2009 | Askew et al. |
| 2010/0057063 A1 | 3/2010 | Arless et al. |
| 2010/0256621 A1 | 10/2010 | Babkin et al. |
| 2010/0256642 A1 | 10/2010 | Stone |
| 2011/0082351 A1 | 4/2011 | Razzaque et al. |
| 2011/0306958 A1 | 12/2011 | Berzak et al. |
| 2012/0007352 A1 | 1/2012 | Nguyen et al. |
| 2012/0316558 A1 | 12/2012 | Hendriks et al. |
| 2013/0103020 A1 | 4/2013 | Levin |
| 2014/0169993 A1 | 6/2014 | Berzak et al. |
| 2014/0194863 A1 | 7/2014 | Berzak et al. |
| 2014/0350537 A1 | 11/2014 | Baust et al. |
| 2015/0126987 A1 | 5/2015 | Semenov et al. |
| 2015/0257810 A1 | 9/2015 | Baust et al. |
| 2015/0300344 A1 | 10/2015 | Berzak et al. |
| 2016/0135864 A1 | 5/2016 | Babkin et al. |
| 2016/0249970 A1 | 9/2016 | Yu et al. |
| 2018/0028251 A1* | 2/2018 | George .............. A61B 18/02 |
| 2019/0175395 A1 | 6/2019 | Kim |
| 2019/0254731 A9 | 8/2019 | Sperling et al. |
| 2019/0290348 A1 | 9/2019 | Clarke |
| 2019/0328437 A1 | 10/2019 | Perron et al. |
| 2019/0390822 A1 | 12/2019 | Brothers |
| 2020/0015750 A1 | 1/2020 | Pike et al. |
| 2020/0121498 A1 | 4/2020 | Baust et al. |
| 2020/0297403 A1 | 9/2020 | Kochavi |
| 2020/0378556 A1 | 12/2020 | Wowk et al. |
| 2021/0161577 A1 | 6/2021 | Johansson |
| 2021/0177482 A1 | 6/2021 | Tegg et al. |
| 2021/0177483 A1 | 6/2021 | Tegg et al. |
| 2021/0239257 A1 | 8/2021 | Stautner |
| 2021/0244457 A1* | 8/2021 | Hilleli .............. A61B 18/0218 |
| 2021/0369319 A1 | 12/2021 | Sprain et al. |
| 2021/0396336 A1 | 12/2021 | Schroeter |
| 2022/0287757 A1 | 9/2022 | Gong et al. |
| 2022/0304737 A1* | 9/2022 | Pang .............. A61B 18/02 |

(56) References Cited

U.S. PATENT DOCUMENTS

| | | |
|---|---|---|
| 2023/0210575 A1 | 7/2023 | Hilleli et al. |
| 2023/0213129 A1 | 7/2023 | Peabody et al. |

FOREIGN PATENT DOCUMENTS

| | | |
|---|---|---|
| CN | 102488550 B | 4/2013 |
| CN | 203122580 U | 8/2013 |
| CN | 203641719 U | 6/2014 |
| CN | 203873871 U | 10/2014 |
| CN | 204219026 U | 3/2015 |
| CN | 104605925 A | 5/2015 |
| CN | 204797984 U | 11/2015 |
| CN | 103784193 B | 12/2015 |
| CN | 207870952 U | 9/2018 |
| CN | 208511163 U | 2/2019 |
| CN | 208541399 U | 2/2019 |
| CN | 109431595 B | 3/2019 |
| CN | 109674525 A | 4/2019 |
| CN | 208677560 U | 4/2019 |
| CN | 208693430 U | 4/2019 |
| CN | 208693431 U | 4/2019 |
| CN | 209032618 U | 6/2019 |
| CN | 109984734 A | 7/2019 |
| CN | 209059412 U | 7/2019 |
| CN | 209153957 U | 7/2019 |
| CN | 209301311 U | 8/2019 |
| CN | 209326130 U | 8/2019 |
| CN | 110236671 A | 9/2019 |
| CN | 209360883 U | 9/2019 |
| CN | 209470383 U | 10/2019 |
| CN | 209574862 U | 11/2019 |
| CN | 209751207 U | 12/2019 |
| CN | 209826947 U | 12/2019 |
| CN | 209826949 U | 12/2019 |
| CN | 209842088 U | 12/2019 |
| CN | 209847361 U | 12/2019 |
| CN | 110251224 B | 2/2020 |
| CN | 210019627 U | 2/2020 |
| CN | 210019628 U | 2/2020 |
| CN | 210056206 U | 2/2020 |
| CN | 211094644 U | 7/2020 |
| CN | 213216941 U | 5/2021 |
| CN | 214010591 U | 8/2021 |
| DE | 202004008875 U1 | 8/2004 |
| EP | 0292922 B1 | 11/1988 |
| EP | 395307 A2 | 10/1990 |
| EP | 570301 A1 | 11/1994 |
| EP | 0550666 B1 | 1/1999 |
| EP | 919197 B1 | 2/2005 |
| EP | 2593028 B1 | 8/2017 |
| EP | 2904986 B1 | 7/2022 |
| GB | 1108905 A | 4/1968 |
| GB | 1473856 A | 5/1977 |
| GB | 1534472 A | 12/1978 |
| GB | 2321531 A | 7/1998 |
| GB | 2336781 A | 11/1999 |
| GB | 2337000 A | 11/1999 |
| GB | 2409815 A1 | 7/2005 |
| JP | 2004041428 A1 | 2/2004 |
| JP | 2004275732 A | 10/2004 |
| JP | 2007167100 A | 7/2007 |
| JP | 2011518614 A | 6/2011 |
| JP | 2012513256 A | 6/2012 |
| JP | 2023504366 A | 2/2023 |
| WO | 8303961 A1 | 11/1983 |
| WO | 9637158 A1 | 11/1996 |
| WO | 9639960 A1 | 12/1996 |
| WO | 9947876 A1 | 9/1999 |
| WO | 200137919 A2 | 5/2001 |
| WO | 200141683 A3 | 6/2001 |
| WO | 200197702 A1 | 12/2001 |
| WO | 0202026 A1 | 1/2002 |
| WO | 0211638 A1 | 2/2002 |
| WO | 03015651 A1 | 2/2003 |
| WO | 2004051409 A2 | 6/2004 |
| WO | 2004060465 A2 | 7/2004 |
| WO | 2004089183 A1 | 10/2004 |
| WO | 2004093635 A2 | 11/2004 |
| WO | 2005000106 A2 | 1/2005 |
| WO | 2005098308 A1 | 10/2005 |
| WO | 2006116457 A2 | 11/2006 |
| WO | 2006127467 A2 | 11/2006 |
| WO | 2007028232 A1 | 3/2007 |
| WO | 2007076123 A2 | 7/2007 |
| WO | 2007086056 A2 | 8/2007 |
| WO | 2007129308 A2 | 11/2007 |
| WO | 2013067421 A2 | 5/2013 |
| WO | 2014068262 A1 | 5/2014 |
| WO | 2014137383 A1 | 9/2014 |
| WO | 2018184938 A1 | 10/2018 |
| WO | 2019077508 A1 | 4/2019 |
| WO | 2021027682 A1 | 2/2021 |
| WO | 2021258840 A1 | 12/2021 |

OTHER PUBLICATIONS

EP Application # 23172909.6 Search Report dated Apr. 17, 2024.
JP Application # 2023115854 Office Action dated May 14, 2024.
U.S. Appl. No. 18/184,693 Office Action dated May 23, 2024.
JP Application # 2023088275 Office Action dated Jun. 4, 2024.
Castillo-Dominguez et al., "Cryostat and CCD for MEGARA at GTC," Conference Paper in Proceedings of SPIE—The International Society for Optical Engineering, pp. 2-11, Sep. 2012.
Douglas, Jr., et al, "Cryosurgical Denervation of the Heart: Acute and Chronic Effects," The Journal of Thoracic and Cardiovascular Surgery, vol. 100, pp. 198-209, year 1990.
Li et al., "A Compact Cryogenic Pump," Elsevier, open-access version, pp. 1-6, year 2015.
Verkin et al., "Low Temperatures in Stomatology," Naukova Dumka, Kiev, pp. 62-63, year 1990.
JP Application # 2022091916 Office Action dated Nov. 22, 2023.
EP Application # 23180921.1 Search Report dated Nov. 22, 2023.
EP Application # 23172909.6 Search Report dated Oct. 5, 2023.
EP Application # 24198646.2 Search Report dated Feb. 12, 2025.
Zhang et al., "Two phase flow characteristics of liquid nitrogen in vertically upward 0.5 and 1.0 mm micro-tubes: Visualization studies", Cryogenics, vol. 49, issue 10, pp. 565-575, Oct. 2009.
Qi et al., "Development and performance test of a cryoprobe with heat transfer enhancement configuration", Cryogenics, vol. 46, pp. 881-887, year 2006.
Qi et al., "Flow boiling of liquid nitrogen in micro-tubes: Part I—onset of nucleate boiling, two phase flow instability and two phase flow pressure drop", International Journal of Heat and Mass Transfer, vol. 50, pp. 4999-5016, year 2007.
Qi et al., "Flow boiling of liquid nitrogen in micro-tubes: Part II—heat transfer characteristics and critical heat flux", International Journal of Heat and Mass Transfer, vol. 50, pp. 5017-5030, year 2007.
JP Application # 202112530 Office Action dated Aug. 23, 2022.
U.S. Appl. No. 16/785,686 Office Action dated Sep. 16, 2022.
EP Application # 22174876.7 Search Report dated Nov. 4, 2022.
U.S. Appl. No. 17/828,128 Non Office Action dated Feb. 21, 2025.
U.S. Appl. No. 17/828,128 Final Office Action dated May 6, 2025.
JP Application # 2024-155459 Office Action dated Jul. 4, 2025.

\* cited by examiner

FIG. 5

CRYOGEN FLOW CONTROL

FIELD OF THE INVENTION

This invention relates generally to cryogen flow, and specifically to controlling the flow of a cryogen efficiently.

BACKGROUND OF THE INVENTION

Pumps for cryogenic materials have to be able to overcome limitations caused by the extreme cold, such as reduced elasticity, so as to operate effectively. Vapor lock is also a problem for cryogenic pumps. Systems and methods for improving the efficiency of cryogenic pumps are known in the art.

U.S. Pat. No. 6,007,571 to Neilson, et al., describes a liquid coolant supply system for supplying a liquid coolant to a thermal therapy catheter. The system has a sensor control unit that includes a pump, a cooling device, a temperature sensor and a pressure sensor.

U.S. Pat. No. 6,471,694 to Kudaravalli, et al., describes a control system for cryosurgery. Procedures are disclosed for bringing the system to a desired operational state, for controlling the operation by controlling refrigerant flow rate, for performing safety checks, and for achieving safe shutdown.

U.S. Pat. No. 6,939,346 to Kannenberg, et al., describes apparatus for controlling a temperature-controlled probe. The apparatus includes a controller coupled to a probe, and a thermal element to vary probe temperature.

U.S. Pat. No. 7,357,797 to Ryba, describes a system for varying return pressure to control tip temperature of a cryoablation catheter. In the system, the distal end of a refrigerant supply line is positioned in a central lumen and is distanced from the catheter tube's distal tip to establish an expansion chamber.

U.S. Pat. No. 7,731,711, to Levin, describes flow in a central lumen of a cryosurgical instrument that has an oscillating character. In the instrument a refrigerant is provided on the internal surface of a distal cryotip in the form of separated portions.

U.S. Pat. No. 7,780,651, to Abboud, et al., describes a cooling system. A console of the system includes a first cooling system directing coolant to a medical device at a first temperature along a coolant supply line and a second cooling system chilling the coolant within the coolant supply line to a temperature below the first temperature before the coolant reaches a connection point.

U.S. Pat. No. 7,921,657 to Littrup, et al., describes a system for cooling an object with a cryogen having a critical point defined by a critical-point pressure and a critical-point temperature. A pressure of the cryogen is raised above a pressure value determined to provide the cryogen at a reduced molar volume that prevents vapor lock.

U.S. Pat. No. 10,098,685 to Lalonde, et al., describes a system that provides feedback data or information relating to lesion depth in myocardial tissue during a cryoablation procedure.

U.S. Pat. No. 10,213,244 to Fourkas, et al., describes a cryogenic needle of a cryogenic system that is coupled to a heater. Power supplied to the heater is used to interpolate performance of the needle and/or operating parameters of the cryogenic system.

U.S. Pat. No. 10,485,602 to Geiselhart, describes a temperature regulator for regulating the temperature of a cryoprobe. The cryoprobe supplies an at least partly liquid refrigerant at a first pressure to an evaporation region such that a coolant evaporates at least temporarily under the presence of a second pressure for cooling a cooling portion of the cryoprobe.

U.S. Pat. No. 10,828,080 to George, et al., describes a method for regulating pressure to lower temperature in a cryotherapy balloon catheter.

U.S. Patent Application 2005/0159735 to Walton, et al., describes an apparatus for automatic operation of a refrigeration system that provides refrigeration power to a catheter for tissue ablation or mapping. A primary refrigeration system can be open loop or closed loop, and a precool loop will typically be closed loop.

U.S. Patent Application 2005/0198972 to Lentz, et al., describes a pressure-temperature control for a cryoablation catheter system. A temperature sensor is mounted at the distal end of a cryo-catheter. A system controller is in electronic communication with both a pressure regulator and the temperature sensor.

U.S. Patent Application 2019/0175395 Kim, et al., describes a device and a method for cooling living tissues for a medical purpose and other purposes. The cooling device comprises: a container configured to accommodate a cooling medium and thermally coupled with the cooling medium by directly contacting the cooling medium.

SUMMARY OF THE INVENTION

An embodiment of the present invention provides apparatus, consisting of:
 a probe, containing a first lumen and a second lumen and having a distal end configured no contact tissue of a living subject;
 a fluid supply coupled to deliver a cryogenic fluid through the first lumen to the distal end of the probe and to receive the cryogenic fluid returning via the second lumen from the probe;
 a temperature sensor located at the distal end;
 a pressure sensor located at a proximal end of the first lumen and configured to measure a pressure of the cryogenic fluid therein; and
 a processor configured to control a rate of delivery of the cryogenic fluid from the fluid supply, so that, when a temperature measured by the temperature sensor is less than a preset guard temperature, the rate of delivery is a preset low rate, and when the temperature measured by the temperature sensor is greater than or equal to the preset guard temperature, the rate of delivery is set in response to a pressure measured by the pressure sensor.

In a disclosed embodiment when the temperature measured by the temperature sensor is greater than or equal to the preset guard temperature, the rate of delivery is set in response to the temperature.

In a further disclosed embodiment when the temperature measured by the temperature sensor is greater than or equal to the preset guard temperature, the rate of delivery is set in response to a preset target temperature greater than the preset guard temperature. Typically, the preset target temperature is in a range from −10° C. to −50° C.

In a yet further disclosed embodiment when the temperature measured by the temperature sensor is greater than or equal to the preset guard temperature, the rate of delivery is less than or equal to a maximum rate of delivery calculated from a preset function of the pressure. Typically, a first derivative of the preset function at the pressure measured by the pressure sensor is negative.

In an alternative embodiment when the temperature measured by the temperature sensor is greater than or equal to the preset guard temperature, the rate of delivery is set in response to the pressure compared to a parametric pressure selected in response to a critical pressure of the cryogenic fluid. Typically, the parametric pressure is greater than the critical pressure.

In a further alternative embodiment the processor is a proportional-integral-derivative (PID) controller. Typically, the PID controller is operated as a PI controller.

There is further provided, according to an embodiment of the present invention, a method, consisting of:
providing a probe, containing a first lumen and a second lumen and having a distal end configured to contact tissue of a living subject;
coupling a fluid supply to deliver a cryogenic fluid through the first lumen to the distal end of the probe and to receive the cryogenic fluid returning via the second lumen from the probe;
locating a temperature sensor at the distal end;
locating a pressure sensor at a proximal end of the first lumen and configuring the sensor to measure pressure of the cryogenic fluid therein; and
controlling a rate of delivery of the cryogenic fluid from the fluid supply, so that, when a temperature measured by the temperature sensor is less than a preset guard temperature, the rate of delivery is a preset low rate, and when the temperature measured by the temperature sensor is greater than or equal to the preset guard temperature, the rate of delivery is set in response to a pressure measured by the pressure sensor.

There is further provided, according to an embodiment of the present invention, apparatus, consisting of:
a probe, containing a first lumen and a second lumen and having a distal end configured to contact tissue of a living subject;
a fluid supply coupled to deliver a cryogenic fluid through the first lumen to the distal end of the probe and to receive the cryogenic fluid returning via the second lumen from the probe;
a temperature sensor located at the distal end;
a pressure sensor located at a proximal end of the first lumen and configured to measure a pressure of the cryogenic fluid therein; and
a processor configured to control a rate of delivery of the cryogenic fluid from the fluid supply, so that, in response to a preset target temperature for the distal end and the pressure measured by the pressure sensor, a temperature measured by the temperature sensor oscillates by a preset amplitude about the preset target temperature.

Typically, the processor is configured to control the rate of delivery of the cryogenic fluid in response to a ratio of the pressure measured by the pressure sensor to a predetermined pressure. The predetermined pressure may be greater than a critical pressure of the cryogenic fluid.

Typically, the rate of delivery is at least a preset minimum rate of delivery.

Typically, the processor is a proportional-integral-derivative controller, and coefficient values of the controller are selected so that the temperature oscillates by the preset amplitude.

Typically, the preset amplitude is between 8° C. and 12° C.

The present disclosure will be more fully understood from the following detailed description of the embodiments thereof, taken together with the drawings, in which:

DETAILED DESCRIPTION OF EMBODIMENTS

Overview

One of the problems that occurs in operation of a cryogenic probe in a cryogenic procedure is the reduced operational efficiency, or even complete failure to operate, of the probe due to vapor lock. Vapor lock, the reduction or even complete cessation in flow rate of a liquid, occurs in a cryogenic system when cryogenic vapor from evaporated cryogenic liquid constricts or halts the flow of the liquid. The reduction in flow prevents the probe from cooling tissue contacting the probe during the procedure. The vapor lock problem is exacerbated if the cryogenic liquid is effectively uncompressible, and this is the case if the probe is operated at a low pressure, very different from the pressure value of the critical point of the cryogen being used. For example, liquid nitrogen has a critical pressure of approximately 33.5 atm (atmospheres) and so is relatively incompressible at pressures in the approximate range of 1-10 atm.

Embodiments of the invention overcome the vapor lock problem for a cryogenic probe, while mostly operating the probe at a relatively low pressure, by configuring the probe to periodically operate for short periods of time at a high pressure, close to the critical pressure of the cryogen, herein assumed to be liquid nitrogen. In these periods the liquid nitrogen is relatively compressible, and is able to flow more freely to relieve any incipient vapor lock.

To realize the high pressure short periods, embodiments of the invention configure the temperature of the distal end of the probe to oscillate about a target temperature, rather than attempting to maintain the distal end at the target temperature. A processor measures a pressure of the cryogen in the probe, as well as a temperature of the distal end. The processor uses the measured temperature and pressure values to control a rate of rotation of a pump of the cryogen, i.e., to control a flow rate at which cryogen is expelled from the pump into the probe, and the processor is configured so that the flow rate—she rate of rotation of she pump—varies in an oscillatory manner, between high and low values of the flow rate.

The oscillations of flow rate provide the short time periods of high pressure described above, as well as the oscillations about the target temperature.

An embodiment of the present invention provides apparatus, consisting of a probe, containing a first lumen and a second lumen and having a distal end configured to contact tissue of a living subject. There is a fluid supply that is coupled to deliver a cryogenic fluid through the first lumen to the distal end of the probe and to receive the cryogenic fluid returning via the second lumen from the probe.

A temperature sensor is located at the distal end of the probe, and a pressure sensor is located at a proximal end of the first lumen. The pressure sensor measures a pressure of the cryogenic fluid flowing in the first lumen.

A processor is configured to control a rate of delivery of the cryogenic fluid from the fluid supply, so that, when a temperature measured by the temperature sensor is less than a preset guard temperature, the rate of delivery is a preset low rate, and when the temperature measured by the temperature sensor is greater than or equal to the preset guard temperature, the rate of delivery is set in response to a target temperature of the distal end and to a pressure measured by the pressure sensor.

DETAILED DESCRIPTION

In the following description, like elements in the drawings are identified by like numerals.

Figure 1:
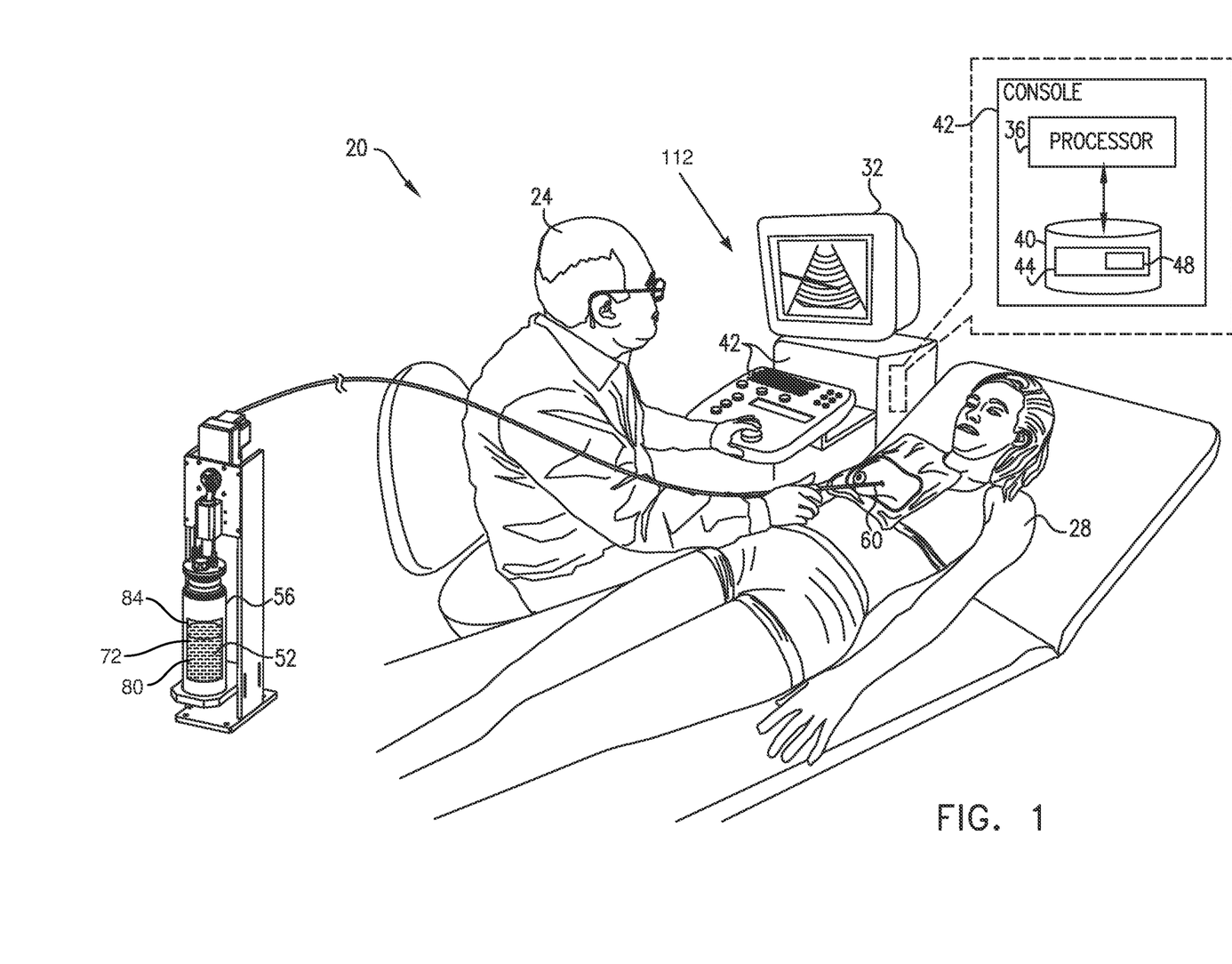
FIG. 1 is a schematic illustration of an apparatus being used for a cryogenic medical procedure, according to an embodiment of the present invention.

Reference is now made to FIG. 1, which is a schematic illustration of an apparatus 20 being used for a cryogenic medical procedure, according to an embodiment of the present invention. By way of example the procedure assumed in the following description is on a breast tumor, but it will be understood that apparatus 20 may be used for other procedures, such as on a prostate or kidney tumor, and all such procedures are considered to be comprised within the scope of the present invention.

The cryogenic procedure on the breast tumor is performed in two phases: a first phase in which a distal end 112 of a probe 60 is reduced in temperature to an temperature, typically between approximately −10° C. and approximately −30° C., and a second phase in which the distal end temperature is further reduced to a subsequent temperature lower than the initial temperature. In one embodiment the subsequent temperature is approximately −160±10° C.

The procedure is performed by a physician 24 on a patient 28, and the physician is able to observe results of the procedure on a display 32 comprised in apparatus 20. (Typically the first phase of the procedure on the breast tumor includes performing an ultrasound scan of the breast of patient 28, and presenting results of the scan on display 32.) The scan is normally performed by an ultrasound professional, other than physician 24. Details of the ultrasound scan are not relevant to the present disclosure, and for simplicity the ultrasound professional is not shown in FIG. 1. Alternatively or additionally, the first phase may include performing a CT (computerized tomography) scan of the breast.)

Apparatus 20 is controlled by a processor 36, which is coupled to a memory 40 wherein is stored software 44 for operation of the apparatus. Processor 36 and memory 40 are installed in an operating console 42. Software 44 in memory 40 may be downloaded to the processor in electronic form, over a network, for example. Alternatively or additionally, the software may be provided on non-transitory tangible media, such as optical, magnetic, or electronic storage media. Software 44 includes software for an apparatus operation algorithm 48, comprising steps executed by the processor in operating apparatus 20. Apparatus operation algorithm 48 is described in more detail below.

In the first and the second phase of the procedure on the breast tumor apparatus 20 is used to inject a cryogenic fluid 52, initially typically held in a pump 56, also herein termed a fluid supply 56, into probe 60 which has distal end 112 inserted into proximity with the tumor. Pump 56 comprises a Dewar 72, which holds cryogenic fluid 52 that is retained in liquid form in a lower space 80 of the Dewar. Above the liquid in the Dewar, in an upper space 84, there is gas formed by evaporation of the cryogenic liquid. A pump similar to pump 56 is described in U.S. patent application Ser. No. 16/785,686 titled "Cryogen Pump" to Hilleli et al., which is incorporated herein by reference.

Fluid 52 is initially in the form of a liquid, but during the procedure the fluid may change from a liquid to a liquid/gas mixture, or even to a completely gaseous state. Except where otherwise stated, cryogenic fluid 52 is herein assumed, by way of example, to comprise liquid or gaseous nitrogen. However, it will be understood that other cryogenic fluids, such as cryogenic argon, may be used in apparatus 20, and all such cryogenic fluids are assumed to be comprised within the scope of the present invention. Pump 56 is connected to probe 60, which physician 24 manipulates so as to correctly position the probe distal end with respect to the tumor. (The manipulation is typically assisted by the physician observing the ultrasound scan referred to above.) Probe 60 is described in more detail below.

Figure 2:
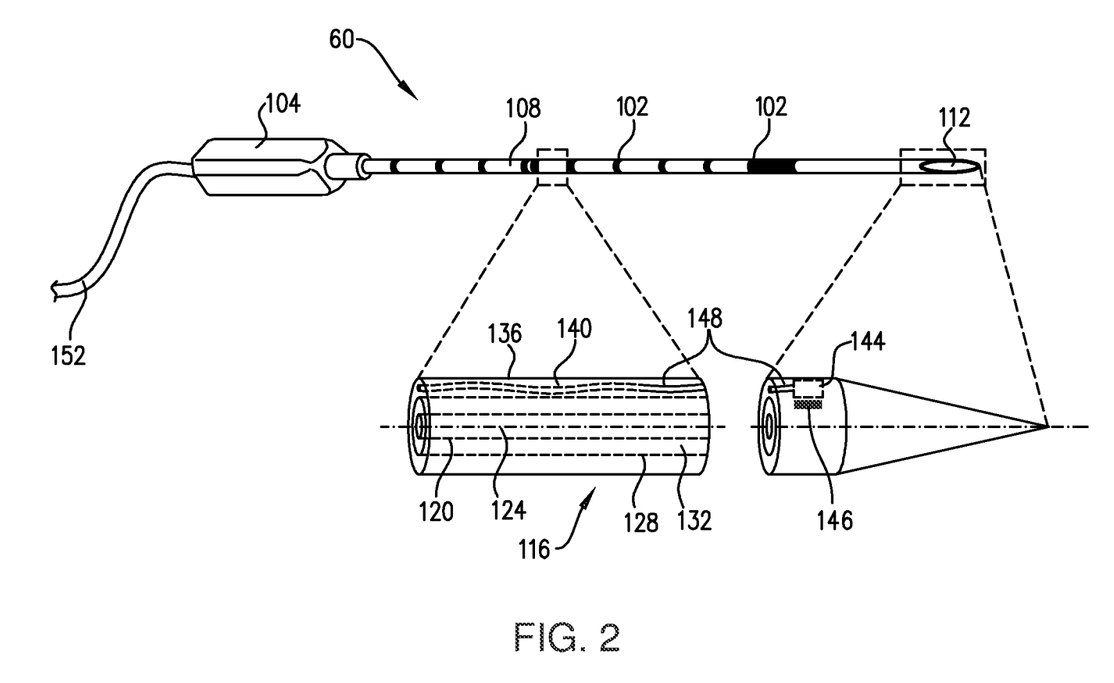
FIG. 2 is a schematic diagram of a probe, according to an embodiment of the present invention.

FIG. 2 is a schematic diagram of probe 60, according to an embodiment of the present invention. Probe 60 comprises a handle 104, which is attached to a shaft 108 of the probe at a shaft proximal end. Shaft 108 terminates in a pointed distal end 112, which enables the shaft to pierce tissue, such as a section of a breast of patient 28. (Markings 102 on an external wall of the shaft indicate distances from the distal end, and may be used by physician 24 in placement of Probe 60 during the procedure.) As shown in a section 116, shaft 108 comprises three concentric tubes, typically formed from thin-walled stainless steel. A first, inner, tube 120 encloses a central lumen 124, and the inner tube is surrounded by a second tube 128. The first tube and the second tube are separated by an intermediate space 132. A third, outer, tube 136 surrounds second tube 128, and the second and third tubes are separated by a space 140. Markings 102 may be placed on an external wall of tube 136.

A temperature sensor 144, typically a thermocouple or a thermistor, is fixedly located within distal end 112, typically in proximity to a heat exchanger 146, surrounding tube 120, that is positioned at the distal end. Cabling 148 for the temperature sensor is typically positioned in space 140. The cabling is connected to processor 36, and enables the processor to measure a temperature sensed by sensor 144.

In operation of apparatus 20, space 140, between the second and third tubes of shaft 108, is maintained in a sealed evacuated state. As is explained in more detail below, central lumen 124 is used to convey cryogenic fluid from pump 56 to distal end 112, and intermediate space 132 is used to return cryogenic fluid from the distal end to the pump.

A flexible tube 152, having an internal structure generally similar to the internal structure of shaft 108, is coupled to the shaft via handle 104. Lumens within tube 152 are configured to convey cryogenic fluid from pump 56 to central lumen 121, and to transfer returning cryogenic fluid from intermediate space 132 to the pump.

Figure 3:
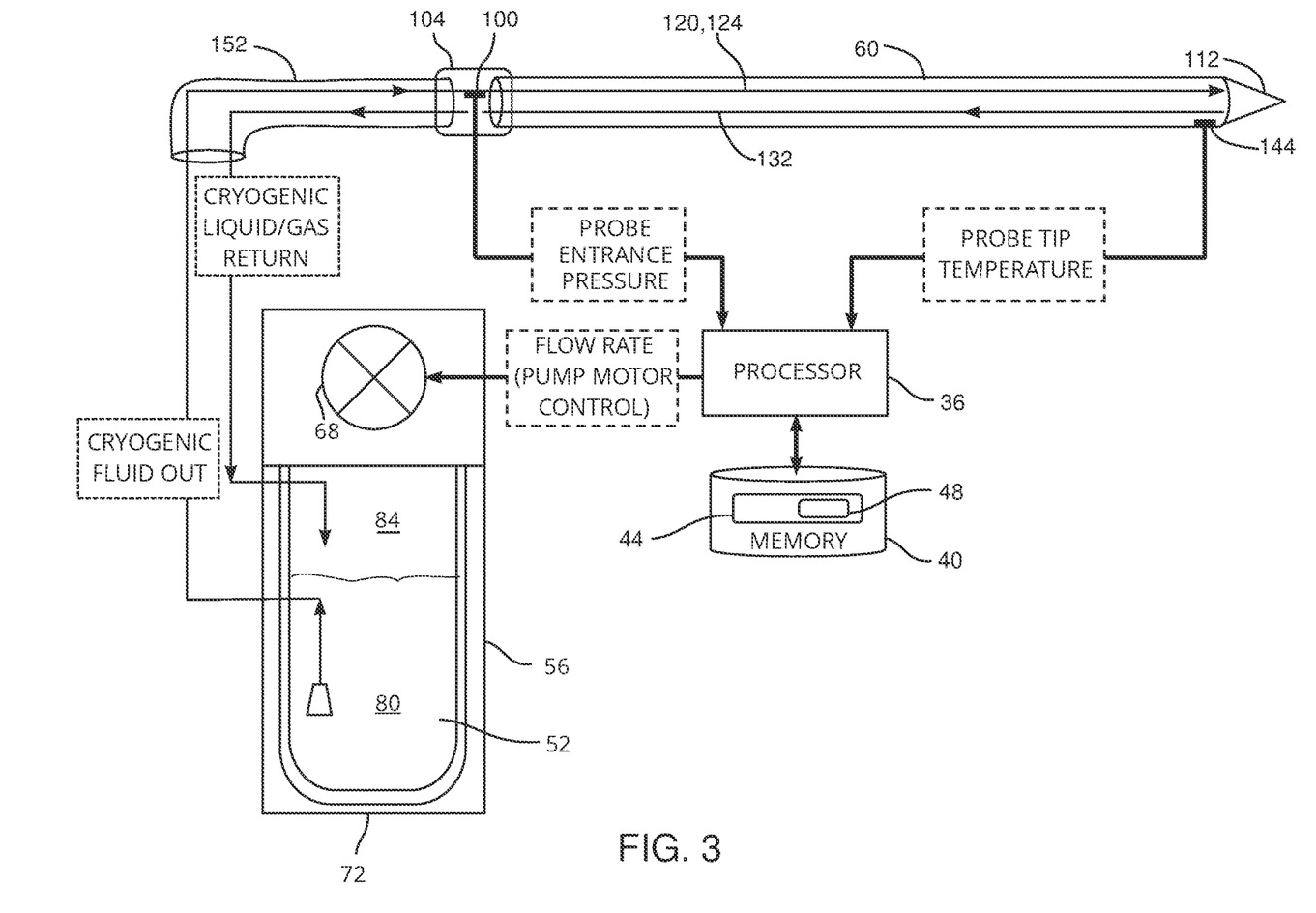
FIG. 3 is a schematic block diagram of apparatus, illustrating how the elements of the apparatus are connected together, according to an embodiment of the present invention.

FIG. 3 is a schematic block diagram of apparatus 20, illustrating how the elements of the apparatus are connected together, according to an embodiment of the present invention. The block diagram illustrates the flow of cryogenic fluid, and the flow of signal data, between the elements.

Processor 36 controls operation of apparatus 20, by providing pump motor control signals to motor 68. On activation, the motor operates pump 56 so that cryogenic fluid is expelled, at a flow rate which depends on the revolution rate of the motor, from Dewar 72. Thus, in the description herein, except where otherwise indicated, the speed of the motor, i.e., the motor's revolution rate, is directly proportional to the flow rate of the expelled cryogenic fluid, so that large revolution rates correspond to large flow rates, and small revolution rates correspond to small flow rates. Flow rate is herein also termed rate of delivery.

In the description herein flow rates are given as rpm (revolutions per minute), and in an embodiment the pump has a motor with a gear ratio of 1:50, so that 3,000 rpm of the motor corresponds to 60 rpm of the pump. When the fluid is 100% liquid an approximate conversion factor for the pump rpm to the flow rate is: 60 rpm=0.36 liters/minute.

The expelled cryogenic fluid flows out of the Dewar, via flexible tube 152, handle 104, and lumen 124 of tube 120, to distal end 112.

In a disclosed embodiment processor 36 is a PID (proportional-integral-derivative) controller.

The cryogenic fluid returns from distal end 112, typically as a liquid/gas mixture, via space 132 in probe 60, handle 104, and flexible tube 152 to Dewar 72.

As indicated in the figure, temperature sensor 144, at the distal end of the probe, provides a signal indicative of the temperature of the probe tip to processor 36. Processor 36 also receives, from a pressure sensor 100 in handle 104, a signal indicative of the pressure of the cryogenic fluid entering lumen 124. Sensor 100 is located in handle 104, typically in proximity to internal tube 120, so that the sensor is in contact with the entering cryogenic fluid.

Processor 36 uses the signals from the pressure sensor and the temperature sensor to operate algorithm 48, which enables the processor to generate an output signal controlling pump motor 68. The output signal that is transferred to the pump motor controls the revolution rate of the motor and thus the flow rate of the cryogenic fluid expelled from Dewar 72.

Figure 4:
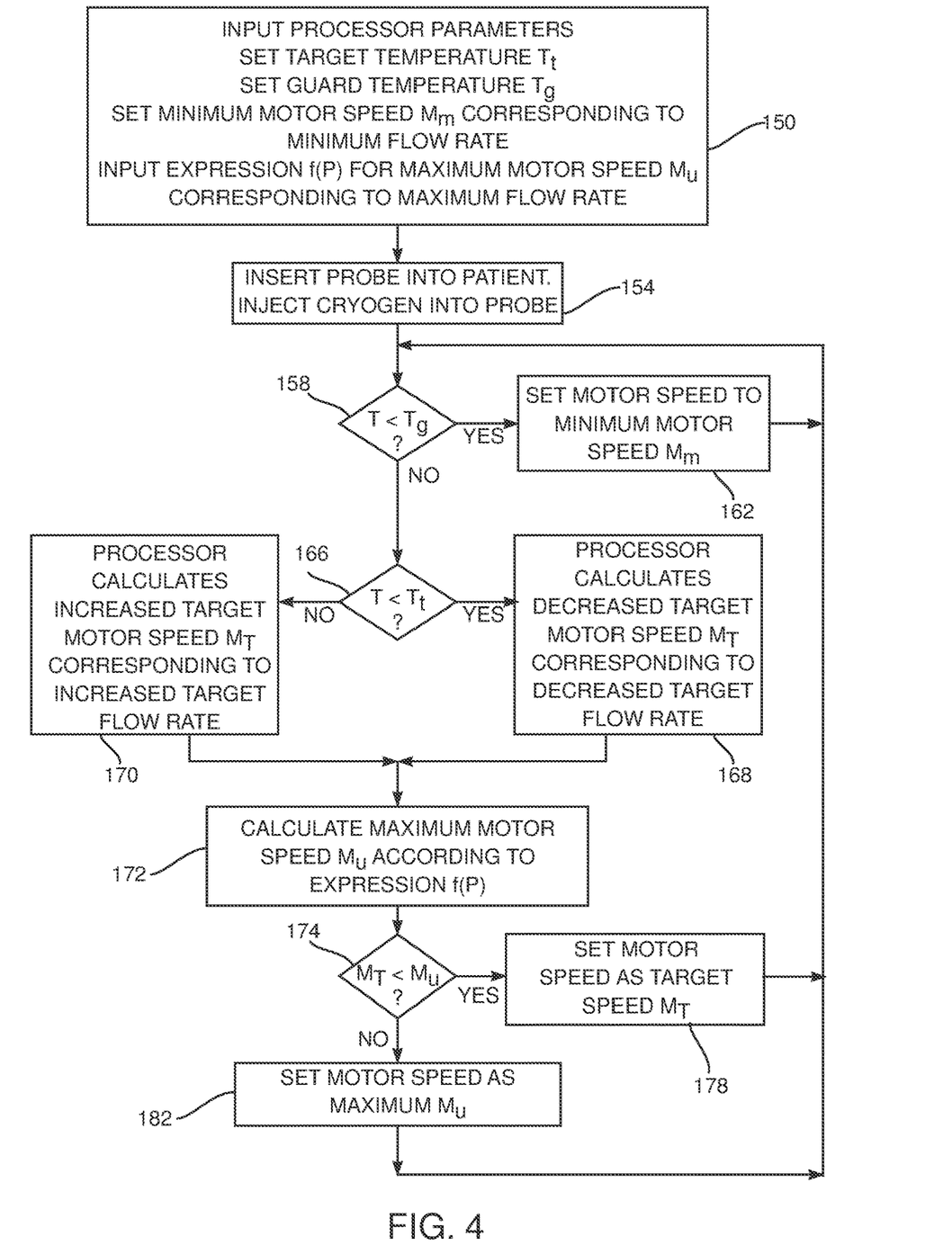
FIG. 4 is a flowchart of operations taken by a processor in executing an algorithm during a first phase of a procedure, according to an embodiment of the present invention.

FIG. 4 is a flowchart of operations taken by processor 36 in executing algorithm 48 during the first phase of the procedure, according to an embodiment of the present invention. In the description of the flowchart, processor 36 is assumed to comprise a. PID (proportional-integral-derivative) controller, having an output given by equation (1):

$$u(t) = K_c \left[ e(t) + \frac{1}{t_i} \int_0^t e(t) dt + t_d \frac{de(t)}{dt} \right] \quad (1)$$

where u(t) is the control signal, output by the processor at time t, and $K_c$, $t_i$, $t_d$ are respective coefficients of the proportional, integral, and differential terms.

A person having ordinary skill in the art will be able to adapt the flowchart description without undue experimentation, mutatis mutandis, for processors other than PID controllers.

In a first step 150, parameters for processor 36, herein, as stated above, assumed to comprise a PID controller, are input to the processor. In the following description the PID controller is assumed to have coefficient values of $K_c$=0.1 and $t_i$=0.05, and $t_d$=0, i.e., processor 36 operates as a PI controller, and those having ordinary skill in the art will be able to adapt the description, without undue experimentation, for other values of $K_c$, $t_i$, and $t_d$.

In step 150 processor 36 is provided with a target temperature $T_t$, which is a nominal temperature to which distal end 112 is cooled. Temperature $T_t$ is typically in a range from −10° C. to −50° C., although in some embodiments $T_t$ is outside this range. Processor 36 is also provided with a guard temperature $T_g$, which is a temperature less than $T_t$, that acts as a nominal temperature limit for the distal end. In one embodiment when $T_t$=−20° C., $T_g$=−23° C.

The processor also sets a minimum motor speed corresponding to a minimum flow rate or a minimum rate of delivery, that the processor applies to pump motor 68 according to steps of the flowchart. In one embodiment the minimum motor speed is set at 224 rpm.

In initial step 150 the processor is also provided with a function f(P) that the processor uses to calculate a maximum motor speed $M_u$, corresponding to a maximum flow rate or a maximum rate of delivery, to be applied to the pump motor, i.e., $$M_u = f(P) \quad (2)$$

where f is a function of pressure P measured by pressure sensor 100.

In an embodiment of the invention f(P) is configured so that if P increases the maximum motor speed $M_u$ falls, so that the maximum flow rate falls, and if P decreases $M_u$ increases, so that the maximum flow rate increases. In the embodiment both derivatives $dM_u/dP$ and $dP/dt$ are negative.

In a disclosed embodiment equation (2) is set as equation (3):

$$M_u = K_1 \cdot \left( 1 - \frac{P}{P_{arb}} \right) \quad (3)$$

where $P_{arb}$ is a parametric pressure having a fixed value that is set to be greater than a critical pressure of the cryogenic fluid being used by apparatus 20; ands $K_1$ is a proportionality constant used to convert the expression on the right side of equation (3) to the units of $M_u$.

From equation (3) the gradient $dM_u/dP$, corresponding to the first derivative of the equation, is given by equation (3a):

$$\frac{dM_u}{dP} = -\frac{K_1}{P_{arb}} \quad (3a)$$

In one example of the disclosed embodiment, when P is measured in psi (pounds per square inch) and $M_u$ is measured in rpm (revolutions per minute), $K_1$=960 rpm and $P_{arb}$=800 psi, so that $$\frac{dM_u}{dP} = -1.2$$

rpm per psi.

In a procedure initialization step 154, physician 24 inserts probe 60 into patient 28, and activates pump 56 to inject cryogenic fluid into the probe.

In a first decision step 158, the processor compares the temperature T measured by sensor 144 with guard temperature by evaluating the expression $$T < T_g \quad (4)$$

If expression (4) returns positive, i.e., temperature T is less than guard temperature T then the processor proceeds to a first set flow rate step 162, wherein the processor sets the motor speed to the minimum speed. $M_m$, corresponding to setting the flow rate to the minimum flow rate. Control then returns to decision step 158.

If expression (4) returns negative, i.e., temperature T is greater than or equal to the guard temperature, then control continues to a second decision step 166. In step 166 the processor compares temperature T with the target temperature $T_t$ by evaluating the expression $$T<T_t \qquad (5)$$

If step 166 returns positive, i.e., temperature T is less than target temperature $T_t$, then in a decrease motor speed step 168, the processor calculates a decreased target motor speed $M_T$, corresponding to a decreased target flow rate.

If step 166 returns negative, i.e., temperature T is greater than or equal to target temperature $T_t$, then in an increase motor speed step 170, the processor calculates an increased target motor speed $M_T$, corresponding to an increased target flow rate.

In steps 168 and 170, the processor evaluates u(t) according to equation (1), and determines the target motor speed. $M_T$ according to equation (6):

$$M_T K_2 u(t) \qquad (6)$$

where $K_2$ is a proportionality constant used to convert u(t) to the units of motor speed.

In a disclosed embodiment, $K_2$=640 rpm.

Control from steps 168 and 170 continues at a maximum speed step 172.

In step 172 the processor accesses the value pressure P provided by pressure sensor 100, and uses the value to calculate the maximum motor speed $M_u$ according to equation (2).

In a third decision step 174, the processor compares the motor speeds $M_T$ and $M_u$, i.e., the processor compares the target flow rate and the maximum flow rate, by evaluating the expression $$M_T<M_u \qquad (7)$$

If expression (7) returns positive, i.e., the target motor speed $M_T$ is less than the maximum motor speed $M_u$, then the processor proceeds to a second set flow rate step 178, wherein the processor sets the motor speed to the target motor speed $M_T$. I.e., the processor sets the flow rate to the target flow rate.

If expression (7) returns negative, i.e., motor speed $M_T$ is equal to or greater than maximum speed $M_u$, then the processor proceeds to a third set flow rate step 182, wherein the processor sets the motor speed to the maximum motor speed $M_u$. I.e., the processor sets the flow rate to the maximum flow rate.

The flowchart of FIG. 4 reiterates by control from the flow rate steps 162, 178, and 182 returning to decision step 158.

The steps of the flowchart, corresponding to algorithm 48, are performed during the first phase of the procedure described with reference to FIG. 1. The first phase terminates when the physician ceases iterating the flowchart steps, i.e., halts operation of algorithm 48. At this point the physician may proceed to the second phase of the procedure, to further lower the temperature of distal end 112. In the second phase algorithm 48 is not activated, and the lower temperature is typically achieved by increasing the flow rate of pump 56.

Figure 5:
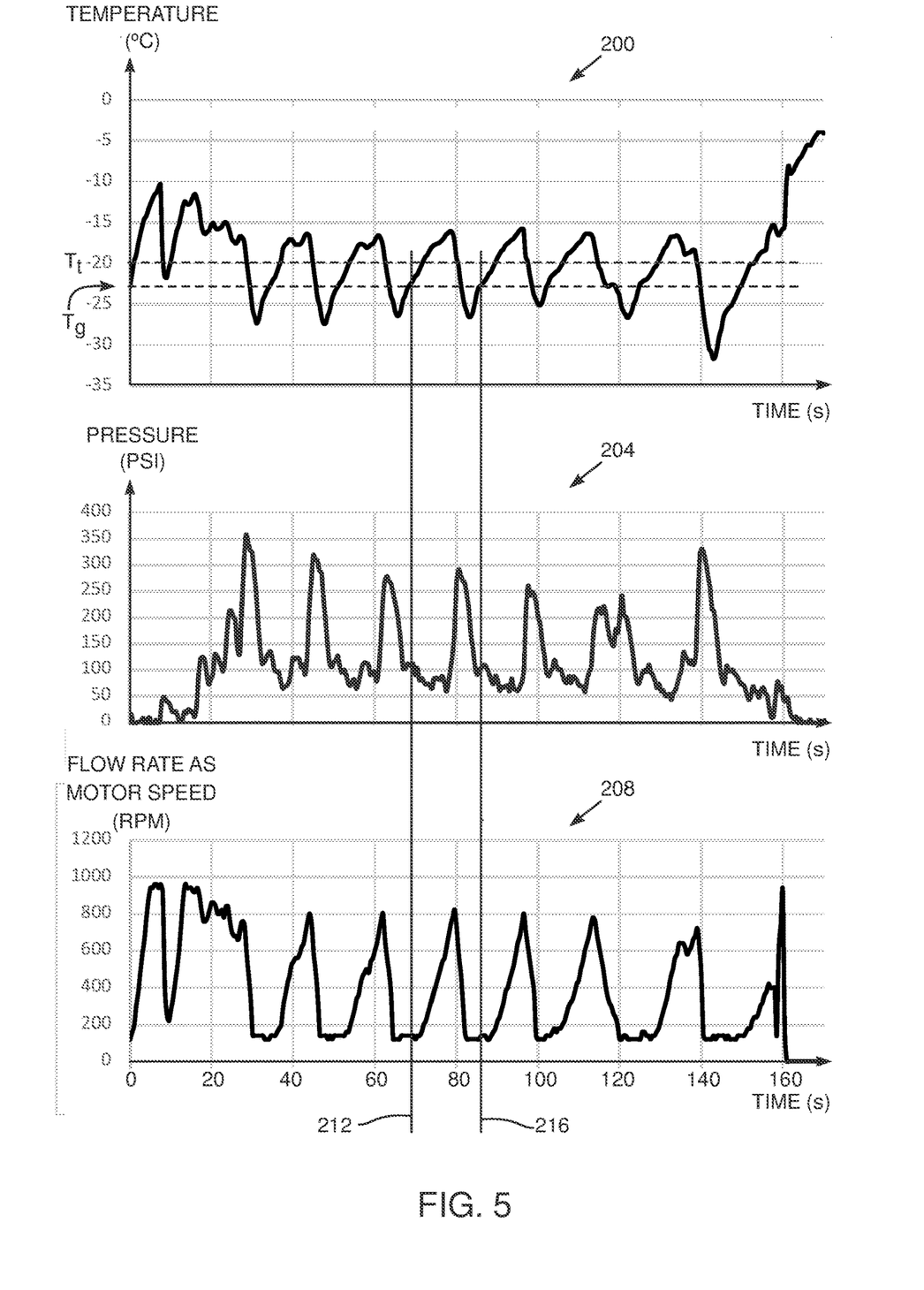
FIG. 5 is a set of schematic graphs obtained during operation of the flowchart of FIG. 4, according to an embodiment of the present invention

FIG. 5 is a set of schematic graphs obtained during operation of the flowchart of FIG. 4, i.e., during activation of algorithm 48, according to an embodiment of the present invention. A first graph 200 plots temperature of distal end 112, as measured by sensor 144, vs. time; a second graph 204 plots pressure, as measured by sensor 100, vs. time; and a third graph 208 plots cryogen flow rate as measured by the pump motor speed, corresponding to the input from processor 36 to pump 68, vs. time.

As is illustrated in the graphs, when the distal end temperature T is below the guard temperature $T_g$, the flow rate and the motor speed are low and approximately constant, corresponding to first flow rate step 162 of the flowchart. The low flow rate allows the distal end temperature to increase above guard temperature $T_g$ and the pressure may also increase. Typically, as is illustrated at a time 212, exiting from guard temperature $T_g$ the pressure is low so that there is a high value for the maximum flow rate and maximum motor speed $M_u$ (calculated in step 172), and because T is less then $T_t$, decision 166 returns positive and the processor begins to decrease the flow rate and motor speed in step 168. Decision 174 then returns positive so this situation corresponds to the second flow rate step 178, where the flow rate is set at the target flow rate by the motor speed being set at the target speed. $M_T$.

However, when T is greater than or equal to $T_t$, the processor begins to increase the target flow rate and target motor speed $M_T$ in step 170. Since the maximum flow rate and maximum motor speed $M_u$ are still high decision 174 returns positive so that second flow rate step 178 still applies, and the increased target flow rate and target motor speed $M_T$, can continue.

The increased flow rate continues until the pressure, because of the increased flow race, sharply increases, as shown, for example, in graph 204 at time 80. The high pressure relieves any incipient vapor lock, since at the high pressure any liquid cryogen is more compressible than at low pressures. Furthermore, near or beyond the critical pressure the cryogen is, or behaves as, a supercritical fluid. Thus, the cryogen flows more easily in the probe.

The increased flow rate also causes the temperature to sharply drop below $T_g$, as shown in graph 200. The increased pressure means that there is now a low value for the maximum flow rate set by the maximum motor speed $M_u$, so that decision 174 returns negative, and third flow rate step 182 applies. The flow rate consequently drops sharply, corresponding to the low maximum motor speed $M_u$, and this flow rate continues to a time 216.

As is apparent from the graphs, the process implemented by processor 36 is an iterative process, and there is one iteration between times 212 and 216. During the iterations, as illustrated by graph 200, the temperature of the distal end oscillates about a target temperature $T_t$. Graph 204 also illustrates that the pressure measured by pressure sensor 100 oscillates between relatively low values of approximately 100 psi and relatively high values of approximately 300 psi. The oscillations of the temperature, pressure, and flow rate are limited, the respective upper and lower limits depending, inter alia, on the minimum flow rate and motor speed $M_m$ set as well as the maximum flow rate and motor speed $M_u$ given by equation (3). Thus, the oscillations also depend on the coefficients of the PID controller terms used in equation (1).

In an embodiment of the invention, the amplitude of the temperature oscillation of the distal end, when it is oscillating about the target temperature $T_t$, is approximately 10° C., wherein the amplitude is the difference in temperature between a distal end local maximum temperature and a distal end local minimum temperature.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "approximately 80%" may refer to the range of values from 64% to 96%.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
a probe, containing a first lumen and a second lumen and having a distal end configured to contact tissue of a living subject;
a fluid supply coupled to deliver a cryogenic fluid through the first lumen to the distal end of the probe and to receive the cryogenic fluid returning via the second lumen from the probe;
a temperature sensor located at the distal end;
a pressure sensor located at a proximal end of the first lumen and configured to measure a pressure of the cryogenic fluid therein; and
a processor configured to control a rate of delivery of the cryogenic fluid from the fluid supply, so that, when a temperature measured by the temperature sensor is less than a preset guard temperature, the rate of delivery is a preset low rate, and when the temperature measured by the temperature sensor is greater than or equal to the preset guard temperature, the rate of delivery is set in response to a pressure measured by the pressure sensor.

2. The apparatus according to claim 1, wherein when the temperature measured by the temperature sensor is greater than or equal to the preset guard temperature, the rate of delivery is set in response to the temperature.

3. The apparatus according to claim 1, wherein when the temperature measured by the temperature sensor is greater than or equal to the preset guard temperature, the rate of delivery is set in response to a preset target temperature greater than the preset guard temperature.

4. The apparatus according to claim 3 wherein the preset target temperature is in a range from −10° C. to −50° C.

5. The apparatus according to claim 1, wherein when the temperature measured by the temperature sensor is greater than or equal to the preset guard temperature, the rate of delivery is less than or equal to a maximum rate of delivery calculated from a preset function of the pressure.

6. The apparatus according to claim 5, wherein a first derivative of the preset function at the pressure measured by the pressure sensor is negative.

7. The apparatus according to claim 1, wherein the processor comprises a proportional-integral-derivative (PID) controller.

8. The apparatus according to claim 7, wherein the PID controller is operated as a PI controller.

9. Apparatus, comprising:
a probe, containing a first lumen and a second lumen and having a distal end configured to contact tissue of a living subject;
a fluid supply coupled to deliver a cryogenic fluid through the first lumen to the distal end of the probe and to receive the cryogenic fluid returning via the second lumen from the probe;
a temperature sensor located at the distal end;
a pressure sensor located at a proximal end of the first lumen and configured to measure a pressure of the cryogenic fluid therein; and
a processor configured to control a rate of delivery of the cryogenic fluid from the fluid supply, so that, when a temperature measured by the temperature sensor is less than a preset guard temperature, the rate of delivery is a preset low rate, and when the temperature measured by the temperature sensor is greater than or equal to the preset guard temperature, the rate of delivery is set in response to a pressure measured by the pressure sensor,
wherein when the temperature measured by the temperature sensor is greater than or equal to the preset guard temperature, the rate of delivery is set in response to the pressure compared to a parametric pressure selected in response to a critical pressure of the cryogenic fluid.

10. The apparatus according claim 9, wherein the parametric pressure is greater than the critical pressure.

11. A method, comprising:
providing a probe, containing a first lumen and a second lumen and having a distal end configured to contact tissue of a living subject;
coupling a fluid supply to deliver a cryogenic fluid through the first lumen to the distal end of the probe and to receive the cryogenic fluid returning via the second lumen from the probe;
locating a temperature sensor at the distal end;
locating a pressure sensor at a proximal end of the first lumen and configuring the sensor to measure a pressure of the cryogenic fluid therein; and
controlling a rate of delivery of the cryogenic fluid from the fluid supply, so that, when a temperature measured by the temperature sensor is less than a preset guard temperature, the rate of delivery is a preset low rate, and when the temperature measured by the temperature sensor is greater than or equal to the preset guard temperature, the rate of delivery is set in response to a pressure measured by the pressure sensor.

12. The method according to claim 8, wherein when the temperature measured by the temperature sensor is greater than or equal to the preset guard temperature, the rate of delivery is set in response to the temperature.

13. The method according to claim 12, wherein when the temperature measured by the temperature sensor is greater than or equal to the preset guard temperature, the rate of delivery is set in response to a preset target temperature greater than the preset guard temperature.

14. The method according to claim 13 wherein the preset target temperature is in a range from −10° C. to −50° C.

15. The method according to claim 11, wherein when the temperature measured by the temperature sensor is greater than or equal to the preset guard temperature, the rate of delivery is less than or equal to a maximum rate of delivery calculated from a preset function of the pressure.

16. The method according to claim 15, wherein a first derivative of the preset function at the pressure measured by the pressure sensor is negative.

17. The method according to claim 11, and comprising using a proportional-integral-derivative (PID) controller to control the rate of delivery.

18. The method according to claim 17, wherein the PID controller is operated as a PI controller.

19. A method, comprising:
providing a probe, containing a first lumen and a second lumen and having a distal end configured to contact tissue of a living subject;

coupling a fluid supply to deliver a cryogenic fluid through the first lumen to the distal end of the probe and to receive the cryogenic fluid returning via the second lumen from the probe;

locating a temperature sensor at the distal end;

locating a pressure sensor at a proximal end of the first lumen and configuring the sensor to measure a pressure of the cryogenic fluid therein; and controlling a rate of delivery of the cryogenic fluid from the fluid supply, so that, when a temperature measured by the temperature sensor is less than a preset guard temperature, the rate of delivery is a preset low rate, and when the temperature measured by the temperature sensor is greater than or equal to the preset guard temperature, the rate of delivery is set in response to a pressure measured by the pressure sensor, wherein when the temperature measured by the temperature sensor is greater than or equal to the preset guard temperature, the rate of delivery is set in response to the pressure compared to a parametric pressure selected in response to a critical pressure of the cryogenic fluid.

20. The method according claim 19, wherein the parametric pressure is greater than the critical pressure.

21. Apparatus, comprising:
a probe, containing a first lumen and a second lumen and having a distal end configured to contact tissue of a living subject;
a fluid supply coupled to deliver a cryogenic fluid through the first lumen to the distal end of the probe and to receive the cryogenic fluid returning via the second lumen from the probe;
a temperature sensor located at the distal end;
a pressure sensor located at a proximal end of the first lumen and configured to measure a pressure of the cryogenic fluid therein; and
a processor configured to control a rate of delivery of the cryogenic fluid from the fluid supply, so that, in response to a preset target temperature for the distal end and the pressure measured by the pressure sensor, a temperature measured by the temperature sensor oscillates by a preset amplitude about the preset target temperature.

22. The apparatus according to claim 21, wherein the rate of delivery is at least a preset minimum rate of delivery.

23. The apparatus according to claim 21, wherein the processor is a proportional-integral-derivative controller, and wherein coefficient values of the controller are selected so that the temperature oscillates by the preset amplitude.

24. The apparatus according to claim 21, wherein the preset amplitude is between 8° C. and 12° C.

25. Apparatus, comprising:
a probe, containing a first lumen and a second lumen and having a distal end configured to contact tissue of a living subject;
a fluid supply coupled to deliver a cryogenic fluid through the first lumen to the distal end of the probe and to receive the cryogenic fluid returning via the second lumen from the probe;
a temperature sensor located at the distal end;
a pressure sensor located at a proximal end of the first lumen and configured to measure a pressure of the cryogenic fluid therein; and
a processor configured to control a rate of delivery of the cryogenic fluid from the fluid supply, so that, in response to a preset target temperature for the distal end and the pressure measured by the pressure sensor, a temperature measured by the temperature sensor oscillates by a preset amplitude about the preset target temperature,
wherein the processor is configured to control the rate of delivery of the cryogenic fluid in response to a ratio of the pressure measured by the pressure sensor to a predetermined pressure.

26. The apparatus according to claim 25, wherein the predetermined pressure is greater than a critical pressure of the cryogenic fluid.

* * * * *